United States Patent
Rauscher

(10) Patent No.: US 6,423,097 B2
(45) Date of Patent: Jul. 23, 2002

(54) ARTIFICIAL FINGER JOINT

(75) Inventor: Markus Rauscher, Allenwinden (CH)

(73) Assignee: Sulzer Orthopedics Ltd., Baar (CH)

( * ) Notice: Subject to any disclaimer, the term of this patent is extended or adjusted under 35 U.S.C. 154(b) by 0 days.

(21) Appl. No.: 09/813,441

(22) Filed: Mar. 20, 2001

(30) Foreign Application Priority Data

Mar. 21, 2000 (EP) ............................................. 00810236

(51) Int. Cl.⁷ ................................................. A61F 2/42
(52) U.S. Cl. ................................ 623/21.16; 623/21.15; 623/23.4; 623/23.39
(58) Field of Search ........................... 623/16.11, 18.11, 623/21.16, 21.15, 21.11, 23.39, 23.4

(56) References Cited

U.S. PATENT DOCUMENTS

| | | | |
|---|---|---|---|
| 3,506,982 A | * | 4/1970 | Steffee ..................... 623/21.16 |
| 3,991,425 A | * | 11/1976 | Martin et al. ............. 623/18.11 |
| 4,131,957 A | * | 1/1979 | Bokros ...................... 623/23.4 |
| 4,231,121 A | | 11/1980 | Lewis |
| 4,944,758 A | | 7/1990 | Bekki |
| 5,047,059 A | * | 9/1991 | Saffar ....................... 623/21.15 |
| 5,674,297 A | | 10/1997 | Lane et al. |

FOREIGN PATENT DOCUMENTS

DE            4337922 A1     5/1995

* cited by examiner

*Primary Examiner*—Jeffrey A. Smith
(74) *Attorney, Agent, or Firm*—Townsend and Townsend and Crew LLP

(57) ABSTRACT

The invention shows an artificial finger joint comprising a convex joint head and comprising a concave joint shell which can be fastened independently of one another with a respective shaft in a bone end and which can be moved in an articulation plane from an extension position with parallel shaft axes into a hyperextension position or into an articulation end position. A guide pin projects out of the joint shell in the direction of its shaft axis and protrudes into a pocket of the joint head, with the pocket having a first abutment for the guide pin in the hyperextension position. A second abutment between the joint shell and the joint head prevents a tilting of the guide pin and shaft of the joint shell about the first abutment in hyperextension position.

12 Claims, 3 Drawing Sheets

Figure 4:
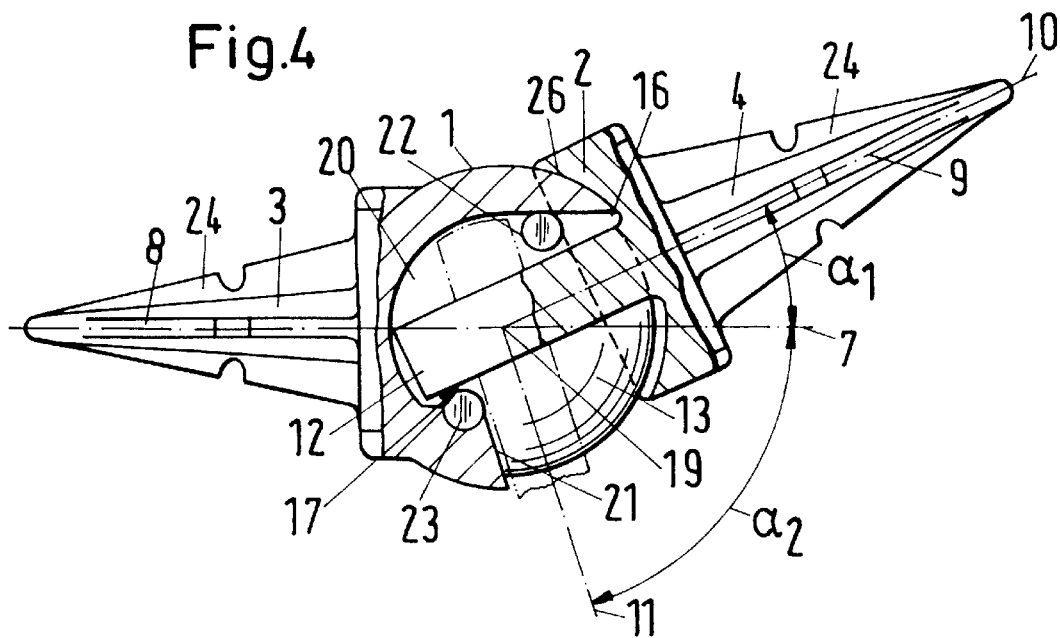

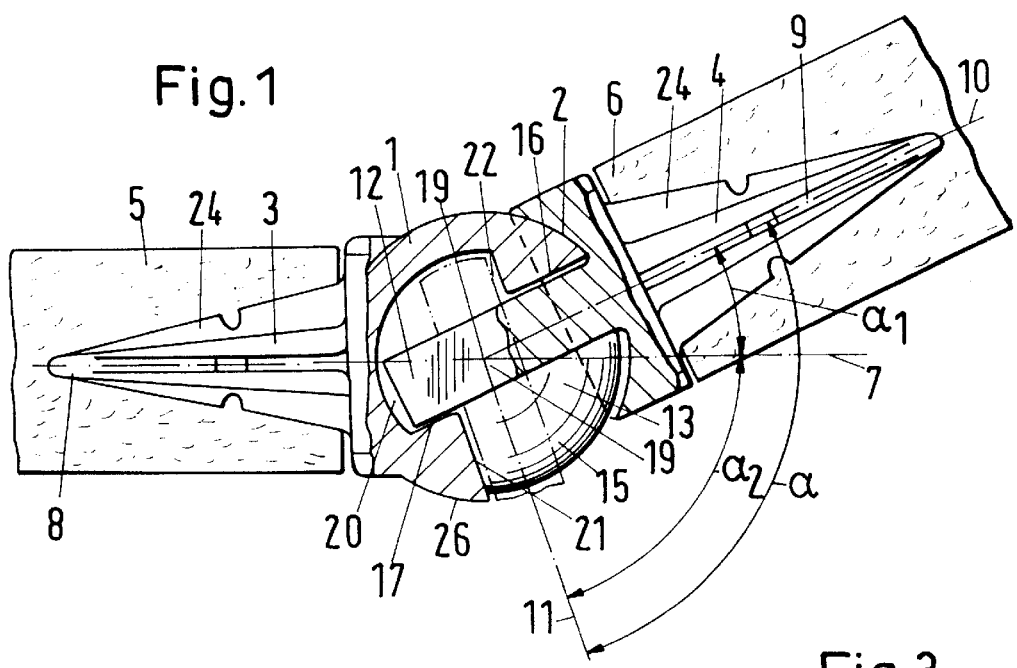
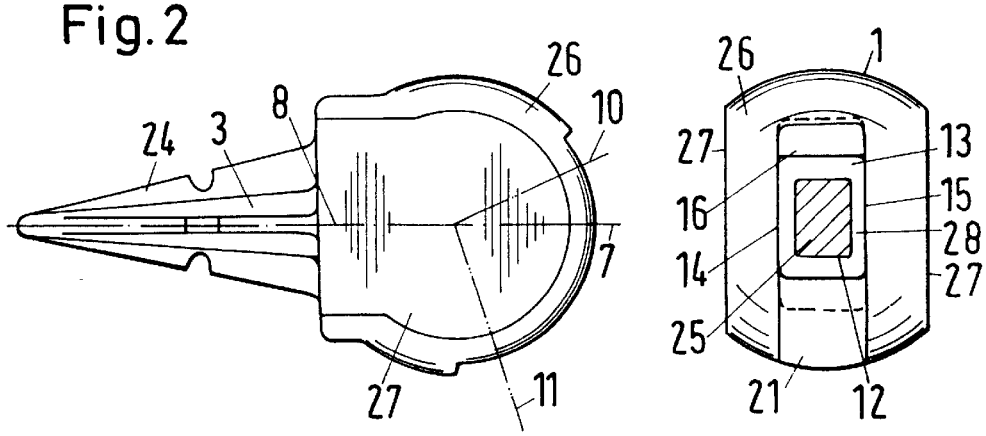
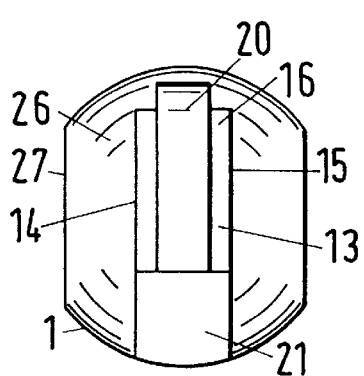
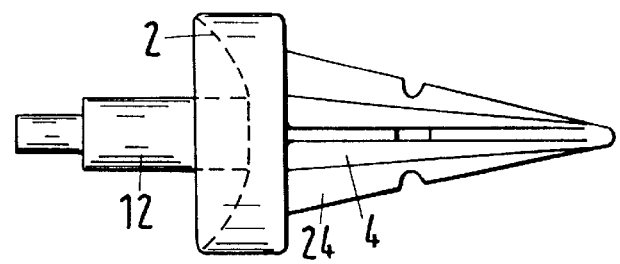

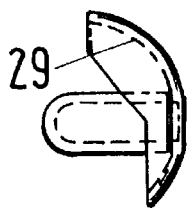
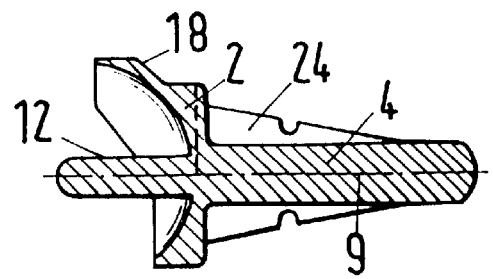
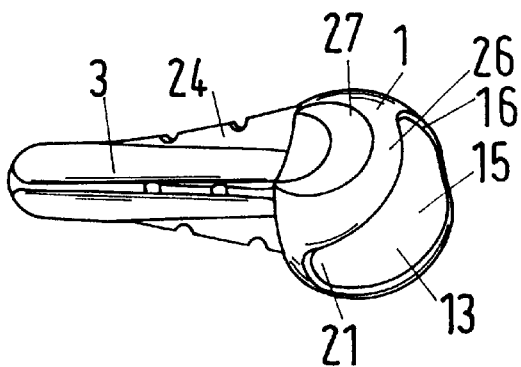
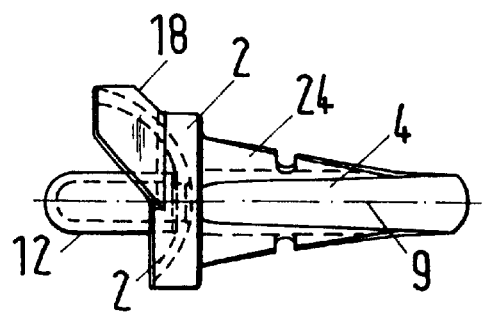
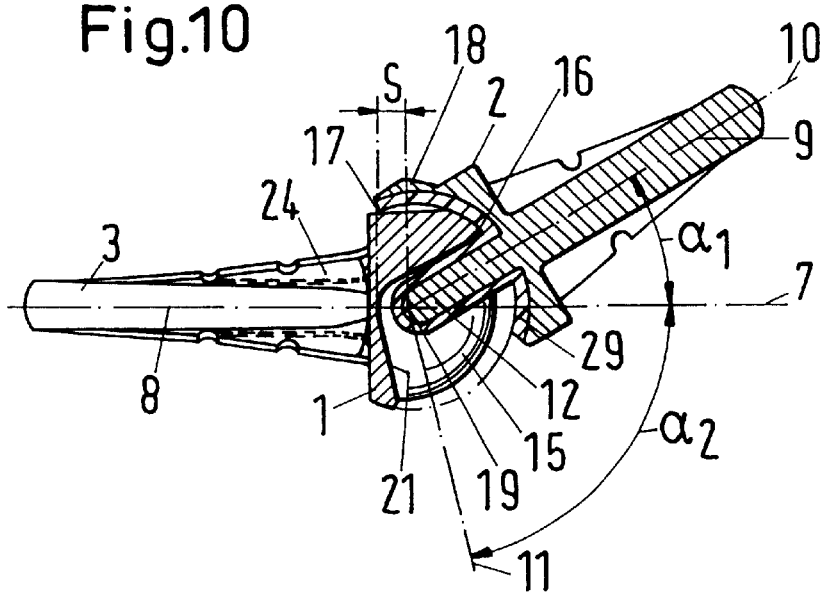

ARTIFICIAL FINGER JOINT

The invention relates to an artificial finger joint comprising a convex joint head and comprising a concave joint shell which can be fastened independently of one another with a respective shaft in a bone end and which can be moved in an articulation plane from an extension position with parallel shaft axes into a hyperextension position or into an articulation end position.

Artificial finger joints occur between the metacarpal bone and the finger bone or between individual finger bones. In order to be able to operate at a finger joint of this kind, the surgeon must expose the bone ends and push aside minute blood vessels, nerves and tendons without overstretching them. It is therefore usual with the lateral pushing aside, which would cause a stretching, to bring the joint into articulation position, in which both bone ends are exposed for a resection. Accordingly it is an advantage when the joint head and the joint pan can be inserted independently of one another and can be brought into engagement as in a natural joint without the above mentioned overstretching arising.

Thus the patent specification U.S. Pat. No. 4,231,121 shows a finger joint which consists of a joint head with a formed on shaft and of a joint shell with a formed on shaft, which can be pushed together in an articulation position. The freedom of movement goes from an extension position into a hyperextension position or into an articulation end position. An embodiment of this kind has the disadvantage that in the end positions, for example in the hyperextension, a sliding off of the joint shell from the joint head can take place when a transverse force arises since the equilibrium state depends substantially on the force with which the two joint parts are held together by the ligaments which surround them.

The object of the invention is to improve artificial finger joints in this regard. This object is satisfied in that a guide pin projects out of the joint shell in the direction of its shaft axis and protrudes into a pocket of the joint head, with the pocket having a first abutment for the guide pin in the hyperextension position; and in that a second abutment is present between the joint shell and the joint head in the hyperextension position and prevents a tilting of the guide pin and the shaft of the joint shell about the first abutment.

The invention has the advantage that, through the provision of a second abutment in a position in which a first abutment is reached for the hyperextension position and would provide a momentary center for a continuation of the rotation, the movement is stopped.

Further advantageous improvements result from the subordinate claims 2 to 12.

Thus it is advantageous that through a corresponding design of the pocket, pivotal angles α from 80° to 130° between the hyperextension position and the articulation end position are possible which lie in the pivotal range of a natural finger joint.

One embodiment provides a cap which is formed on at the joint shell in the direction of the hyperextension position and which when the hyperextension position is reached encounters a second abutment at the joint head which is displaced by a distance S beyond a point of rotation at the joint head in the direction towards the shaft of the latter. An advantage of this cap is that it holds specific ligaments at a distance and is at the same time guided by these ligaments. The guide pin can project from the joint shell as a round pin, which is simple in the manufacturing technology. A further advantage of this cap consists in that the palmar luxation is suppressed in a grasping movement.

A further embodiment provides for the pocket having beyond a point of rotation an undercut extension with a second abutment which is arranged oppositely to the first abutment in order to stop the guide pin, which is extended beyond the point of rotation, when it encounters the first abutment. This embodiment has the advantage that the second abutment lies within the joint head and can not disturb externally.

Between the guide pin and the pocket, a clearance from the lateral guiding cheeks can be provided which amounts to more than 5% of the width of the guide pin in order to enable an articulation in a laterally slightly angled off position of the shaft axes. This has the advantage that fingers can articulate parallel to one another in spite of the splay position of the metacarpal bone.

With a rectangular cross-section of the guide pin the clearance from the guiding cheeks can be adjusted in such a manner that a rotational securing is achieved through a rectangular diagonal which is longer than the spacing of the guiding cheeks. A guide pin which is reduced by the amount of the clearance from the guiding cheeks has the advantage that the degrees of freedom as in a natural finger joint are present for the joint movements.

A further advantage consists in that the bearing surfaces of the joint head and the bearing shell are congruent in the hyperextension position in order to be able to take up the greatest bearing forces in this position, that the curvature of the joint head may however increase in the articulation direction in order not to tension the ligaments too strongly during the articulation.

Analogously to the restriction of the movement in the hyperextension, a third abutment can be provided in the articulation end position and a tilting about this third abutment can be prevented through a fourth abutment, which for example is likewise provided in the pocket and acts on the guide pin.

In order to realize a pocket with undercut abutments in a simple manufacturing technology, a pocket without undercuttings can first be produced in which subsequently provided bolts form the undercuttings and the abutments. The joint head and the joint shell are advantageously manufactured of body compatible metals, for example of titanium or titanium alloys or cobalt-chromium-molybdenum alloys. The frictional relationships between the articulation surfaces can be improved when one of the surfaces consists of plastic, for example of polyethylene or PEAK (polyaryl ether ketone).

Figure 5:
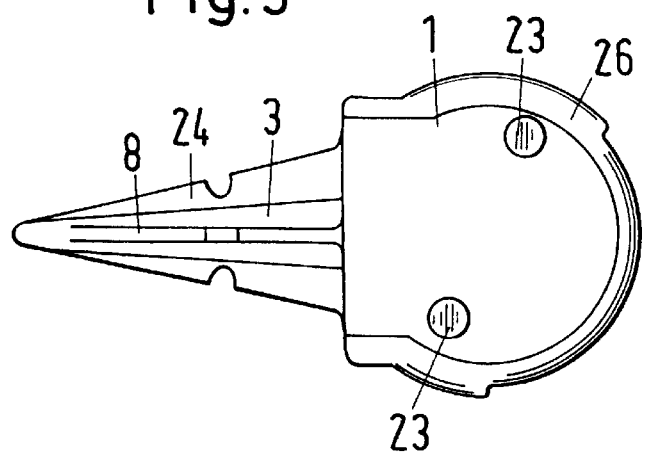
Figure 6:
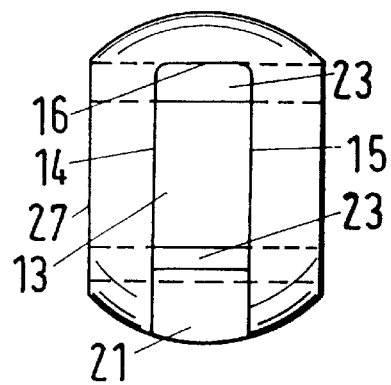
Figure 7:
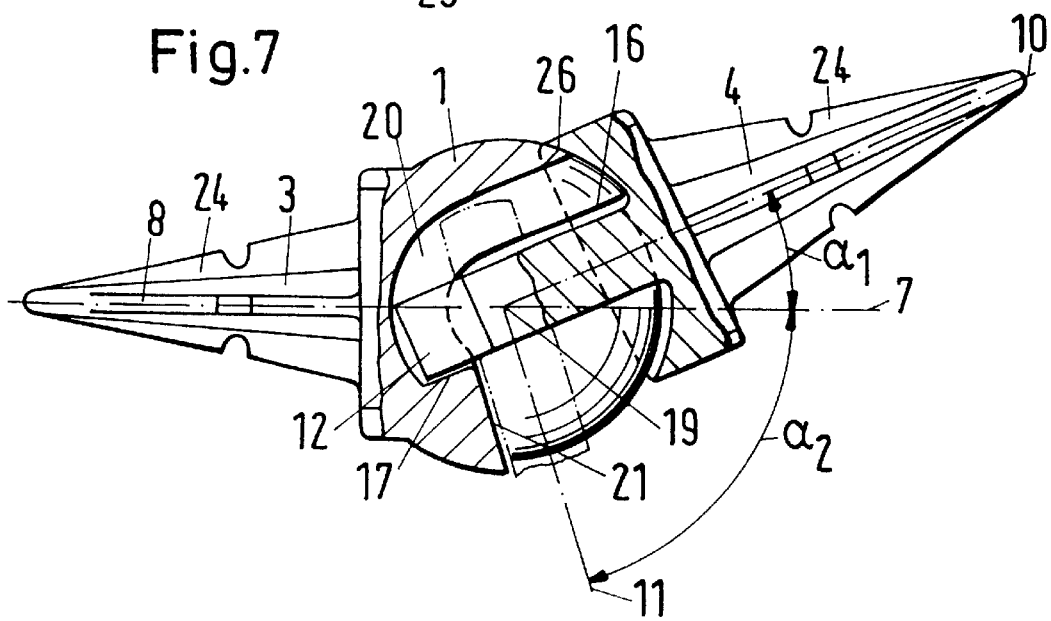

In the following the invention will be illustrated with reference to exemplary embodiments. Shown are:

FIG. 1 schematically, a highly enlarged longitudinal section of an artificial finger joint in accordance with the invention in the hyperextension position;

FIG. 2 schematically, a side view of the joint head of FIG. 1;

FIG. 3 schematically, a view of the end side of the joint head of FIG. 2 with a rectangular guide pin which protrudes into the pocket;

FIG. 4 schematically, a longitudinal section analogous to FIG. 1 in which abutments for a guide pin are formed by subsequently inserted bolts;

FIG. 5 schematically, a side view of the joint head of FIG. 4;

FIG. 6 schematically, a view of the end side of the joint head of FIG. 5;

FIG. 7 schematically, a further solution analogous to FIG. 1 in which the joint head can be manufactured as an injection molded part with a mold separation perpendicular to the hyperextension;

FIG. 8 schematically, a view of the end side of the joint head of FIG. 7;

FIG. 9 schematically, a side view of the joint shell and the guide pin of FIG. 8;

FIG. 10 schematically, a longitudinal section through a further embodiment of an artificial finger joint with a cap which is formed on at the joint shell;

FIG. 11 schematically, a view of the joint head of FIG. 10;

FIG. 12 schematically, a bearing surface which is manufactured as a plastic part and which can be pushed on at the joint shell of FIG. 10;

FIG. 13 schematically, the joint shell of FIG. 10 with reduced dimensions for the reception of the plastic part in FIG. 12; and FIG. 14 schematically, a side view of the joint shell of FIG. 10.

The figures of the exemplary embodiment show an artificial finger joint comprising a convex joint head 1 and a concave joint shell 2 which can be fastened independently of one another with a respective shaft 3, 4 at a bone end 5, 6 and can be moved in an articulation plane from an extension position 7 with parallel shaft axes 8, 9 into a hyperextension position 10 or into an articulation end position 11. A guide pin 12 projects from the joint shell 2 in the direction of the shaft axis of the latter and protrudes into a pocket 13 of the joint head 1, with the pocket 13 having a first abutment 16 for the guide pin 12 in the hyperextension position 10. A second abutment 17 between the joint shell 2 and the joint head prevents in the hyperextension position 10 a tilting of the guide pin 12 and the shaft 4 of the joint shell 2 about the first abutment 16.

In the following, identical reference symbols are used for identical functions.

In the exemplary embodiment of FIGS. 1, 2 and 3 the joint head 1 is anchored with a shaft 3 in a bone end 5. The anchoring is assisted through ribs 24 at the shaft 3. The joint head 1 is provided with a spherical bearing surface 26, the center 19 of which forms a point of rotation on the shaft axis 8. The side surfaces of the joint head 1 have a flattening 27. A pocket 13 with lateral guide cheeks 14, 15 is worked in into the joint head 1. In the hyperextension position 10 of the joint shell 2 the pocket 13 forms a first abutment 16 for the guide pin 12, which projects from the joint shell 2 in the direction of its shaft axis 9, and in the articulation end position 11 a third abutment 21 for the guide pin 12. The pocket 13 is undercut and has an extension 20. Within this extension 20 the guide pin 12, which is prolonged beyond the point of rotation 19, can co-rotate and encounters in the hyperextension position 10 a second abutment 17, which is rotated by 180° with respect to the first abutment 16 and prevents a tilting of the guide pin 12 and its associated shaft 4 about the first abutment 16. The situation is similar in the articulation end position, in which a fourth abutment 22 prevents a tilting about the third abutment 21. The joint shell 2 rotates with its concave bearing shell about the center 19. It is likewise anchored with a shaft 4 and with ribs 24 in a bone end 6. The joint shell can be moved out of an extension position, in which both shaft axes align with one another in their projection (FIG. 1) by a partial angle $\alpha_1$ into a hyperextension position 10 or by a partial angle $\alpha_2$ into an articulation end position 11, with the movement in each case being limited by two cooperating abutments 16, 17; 21, 22. The pivotal angle $\alpha$ of the joint corresponds to the sum of $\alpha_1$ and $\alpha_2$ and amounts to for example 110°.

In FIG. 3 the cross-section 25 of a rectangular guide pin 12 is drawn in which has a total clearance 28 from the guide cheeks 14, 15 of the pocket 13 which corresponds to 40% of the shaft thickness. Nevertheless the rectangular cross-section prevents with a diagonal, which is longer than the spacing of the guide cheeks 14, 15, an extreme rotation of the guide pin 12 and of its associated shaft 4 about the shaft axis 9.

The manufacture of the extension 20 of the pocket 13 can be carried out in different ways. In a guide pin 12 with round cross-section the extension 20 can be pre-bored and then machined to a finish with a finger milling machine. Another possibility consists in securing one guide cheek 14 to the joint head 1 only after the production of the extension 20. A further possibility is shown in FIGS. 4, 5 and 6.

In FIGS. 4, 5 and 6 the joint head 1 is conceived as an injection molded part. The shaft 3, the ribs 24 and the joint head 1 are provided in a single piece. The pocket 13 and its extension 20 are dimensioned without undercutting for a mold removal in the direction of the shaft axis 8. The first abutment 16 and the third abutment 21 are formed by boundaries of the pocket 13. The second abutment 17 for the hyperextension position 10 is formed by a subsequently introduced bolt 23. Likewise the fourth abutment 22 for the articulation end position 11 is formed by a subsequently introduced bolt 23. With two bolts 23 all abutments 16, 21, 17, 22 could in principle be realized with the bolts; but then however the lever arm for a torque which is to be taken up becomes shorter. The joint shell 2 with the guide pin 12 can be formed the same as in FIG. 1.

In FIGS. 7, 8 and 9 an injection molded part without bolts is proposed for the joint head 1, with a fourth abutment being omitted. A slit-shaped extension 20 of the pocket 13 forms an undercutting in the direction of the extension 7 with a second abutment 17 for the hyperextension position 10, with a mold removal being possible in the direction of the hyperextension. The guide pin 12, which projects beyond the point of rotation 19, has been reduced in width at its tip in order to be able to engage into the slit-shaped extension 20 and to encounter the second abutment 17 in the hyperextension position, whereas the first abutment 16 is formed by the shoulders for the wider part of the guide pin 12 which remain adjacently to the slit. In the normally more weakly stressed articulation end position 11 there is a third abutment 21, which does not completely exclude a tilting about this abutment. The securing elements, the shafts 3, 4 and the ribs 24 as well as the outer dimensions are formed as in FIG. 1.

A further embodiment for an artificial finger joint is shown in FIGS. 10 to 14. A joint head 1 with a shaft 3 having a shaft axis 8 and with ribs 24 is provided. It forms a spherical bearing surface 26 with a point of rotation 19. The side surfaces are provided with flattenings 27. A pocket 13, which reaches from the hyperextension position 10 up to the articulation end position 11, forms lateral guide cheeks 15 and a first abutment 16 and a third abutment 21 for a guide pin 12, which protrudes out of the joint shell 2 into the pocket 13. FIG. 12 shows a plastic injection molded part which can be pushed on onto a joint shell 2 in FIG. 13 as a plastic bearing surface 29. The thus pushed together joint shell 2 (FIG. 14) can be anchored with a shaft 4 and ribs 24. The guide pin 12 projects in the direction of the shaft axis 9 of the joint shell 2. A cap 18 is formed on at the actual bearing shell in the direction of the hyperextension. In the hyperextension position 10 (FIG. 10) of the bearing shell 2 and the joint head 1 this cap 18 projects by an amount S beyond the point of rotation 19 in its projection onto the shaft axis 8 of the joint head and encounters at the outer contour of the joint head a second abutment 17, which prevents a tilting about the first abutment 16. The joint shell 2 can be pivoted out of an extension position 7, in which the projected shaft ends 8, 9 coincide, by a partial angle $\alpha_1$ into the hyperextension position 10 or by a partial angle $\alpha_2$ into the articulation end position 11. The sum of the two partial angles lies between 100° and 110°. The cap 18 is cut off laterally in analogy with the flattenings 27. This has the advantage that the lateral ligaments can form a rotational securing about the shaft axis 9.

What is claimed is:

1. Artificial finger joint comprising a convex joint head and a concave joint shell which can be fastened to respective bones independently of one another, each of the joint head and the joint shell with a respective shaft in a bone engaging end and which can be moved in an articulation plane from an extension position with parallel shaft axes into a hyperextension position or into an articulation end position, characterized in that a guide pin projects out of the joint shell in the direction of the shaft axis of the joint shell and protrudes into a pocket of the joint head, with the pocket having a first abutment for the guide pin in the hyperextension position; in that a second abutment is present between the joint shell and the joint head in the hyperextension position and prevents a tilting of the guide pin and the shaft of the joint shell about the first abutment; and in that the guide pin is unrestrained and moveable in the direction of the shaft axis of the joint shell in any possible relative angular position of the joint shell and the joint head.

2. Artificial finger joint in accordance with claim 1, characterized in that the pocket permits a pivotal angle $\alpha$ between 80° and 130° between the hyperextension position and the articulation end position.

3. Artificial finger joint in accordance with claim 1, characterized in that the concave joint shell has in the direction of the hyperextension position a formed on cap which when the hyperextension position is reached encounters a second abutment at the joint head which is displaced by a distance S from a point of rotation in the joint head in the direction towards the shaft of the latter.

4. Artificial finger joint in accordance with claim 1, characterized in that beyond a point of rotation the pocket has an undercut extension with a second abutment which is arranged oppositely to the first abutment; and in that the guide pin protrudes outwardly beyond the point of rotation into the undercut extension.

5. Artificial finger joint in accordance with claim 1, characterized in that the guide pin has a round cross-section and a lateral total clearance of more than 5% of its diameter from guide cheeks of the pocket.

6. Artificial finger joint in accordance with claim 1, characterized in that the guide pin has a rectangular cross-section and has a lateral total clearance of more than 5% of its width from guide cheeks of the pocket.

7. Artificial finger joint in accordance with claim 6, characterized in that the rectangular cross-section has a diagonal which is longer than the spacing of the guide cheeks in order to achieve a rotational securing.

8. Artificial finger joint in accordance with claim 1, characterized in that the convex bearing surface of the joint head and the concave bearing surface of the joint shell are congruent in the hyperextension position; and in that the curvature of the convex bearing surface of the joint head increases in the direction of the articulation.

9. Artificial finger joint in accordance with claim 1, characterized in that a third abutment in the pocket restricts the movement of the guide pin in the articulation end position; and in that a fourth abutment is present in the pocket which prevents a tilting of the guide pin and its shaft about the third abutment.

10. Artificial finger joint in accordance with claim 1, characterized in that abutments are formed as bolts which are subsequently fastened into the pocket.

11. Artificial finger joint in accordance with claim 1, characterized in that the joint head and the joint shell with their shafts consist of metal.

12. Artificial finger joint in accordance with claim 1, characterized in that the joint head or the joint shell have articulation surfaces which consist of plastic.

* * * * *